US00PP32286P2

(12) United States Plant Patent
Van Swieten

(10) Patent No.: US PP32,286 P2
(45) Date of Patent: Oct. 6, 2020

(54) ***PHALAENOPSIS* ORCHID PLANT NAMED 'PHALGASCIJ'**

(50) Latin Name: ***Phalaenopsis* hybrid**
Varietal Denomination: PHALGASCIJ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/873,197

(22) Filed: Feb. 25, 2020

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGASCIJ', particularly characterized by having copper, striped flowers with red-purple lips, apical lobes with bump and ridge, oblong lateral lobes, and is propagated by meristem tissue culture, is disclosed.

3 Drawing Sheets

Genus and species: *Phalaenopsis* hybrid.
Variety denomination: 'PHALGASCIJ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGASCIJ'.

The new *Phalaenopsis* plant is a product of a planned breeding program conducted by the inventor in Bleiswijk, the Netherlands. The objective of this breeding program was to create a new *Phalaenopsis* plant with attractive copper, striped flowers with red-purple lips, suitable for potted plant production.

The new *Phalaenopsis* plant 'PHALGASCIJ' is a result of cross-pollination made by the inventor in March 2010 in Bleiswijk, the Netherlands, of the proprietary female, or seed parent, *Phalaenopsis* hybrid '22286-05' (unpatented) with the proprietary male, or pollen parent, *Phalaenopsis* hybrid '01-3705' (unpatented).

The new *Phalaenopsis* was selected by the inventor as a single plant within the progeny of the stated cross-pollination in a controlled greenhouse in Bleiswijk, the Netherlands, in December 2010. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 25, 2018, by Applicant who obtained the subject matter disclosed directly from the inventor. 'PHALGASCIJ' has not been made publicly available or sold anywhere in the world prior to the effective filing date of this application with the exception of sales or disclosures made one year or less before the effective filing date of this claimed invention by Applicant who obtained 'PHALGASCIJ' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGASCIJ' as a new and distinct variety of *Phalaenopsis* plant:

1) Copper, striped flowers with red-purple lips;
2) Apical lobe has bump and ridge; and
3) Lateral lobe is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in January 2020. Colors in the photographs may differ from the color values cited in the detailed botanical description, which accurately describe the actual colors of the new variety.

DESCRIPTION OF THE NEW VARIETY

Figure 1:
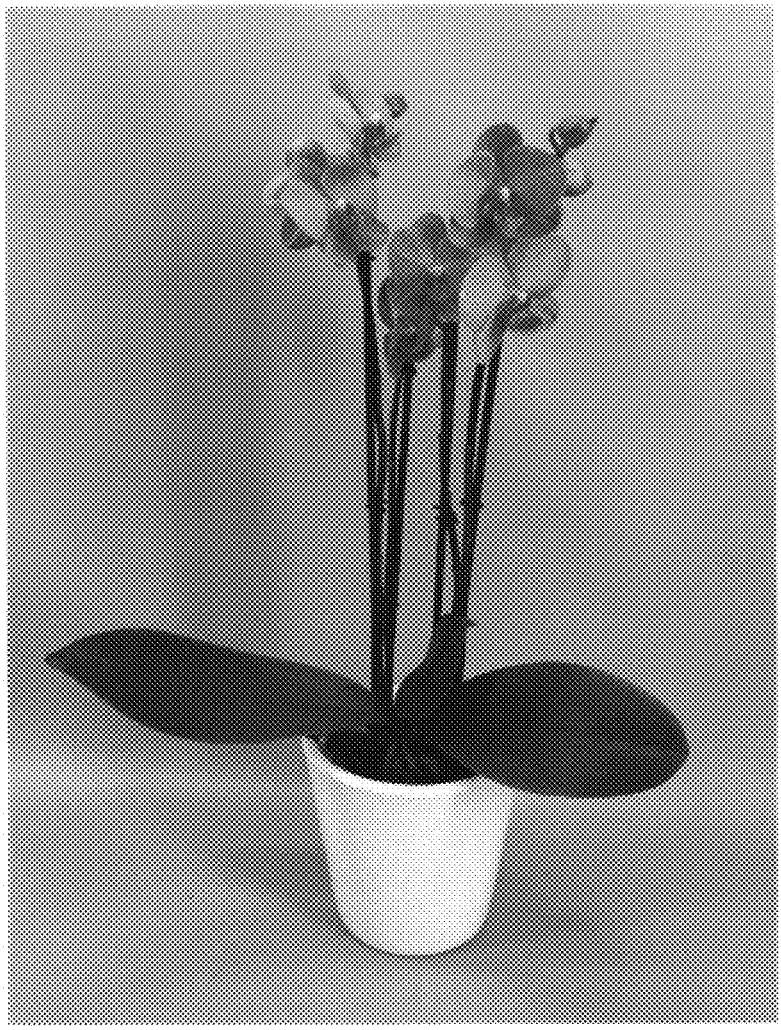
FIG. 1 shows the overall plant habit, including blooms, buds, and foliage of 'PHALGASCIJ'.
Figure 2:
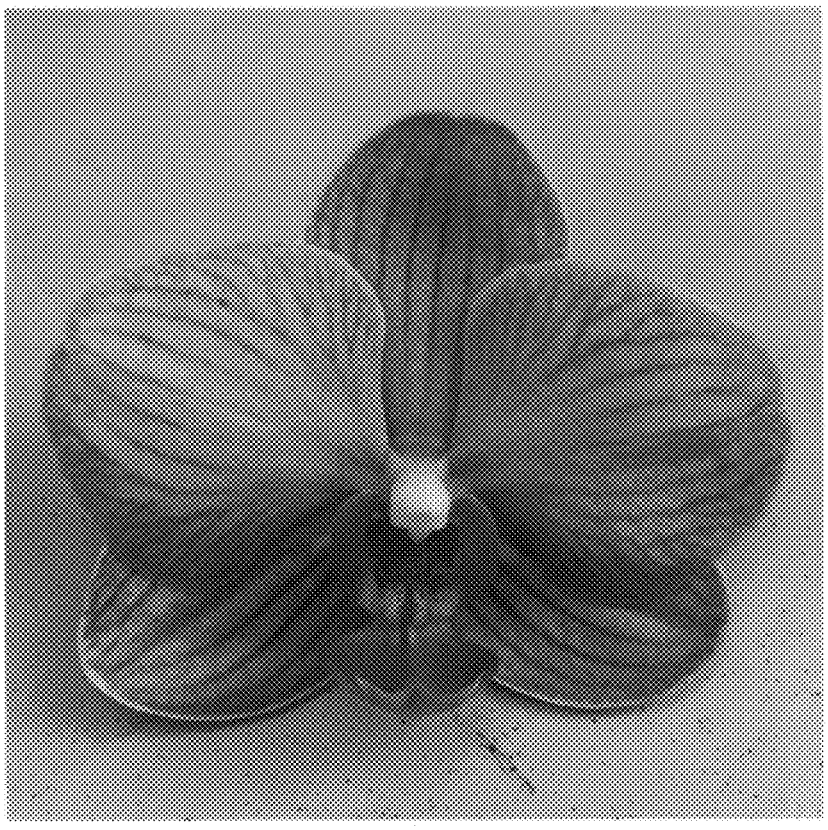
FIG. 2 shows a close-up of a flower of 'PHALGASCIJ'.
Figure 3:
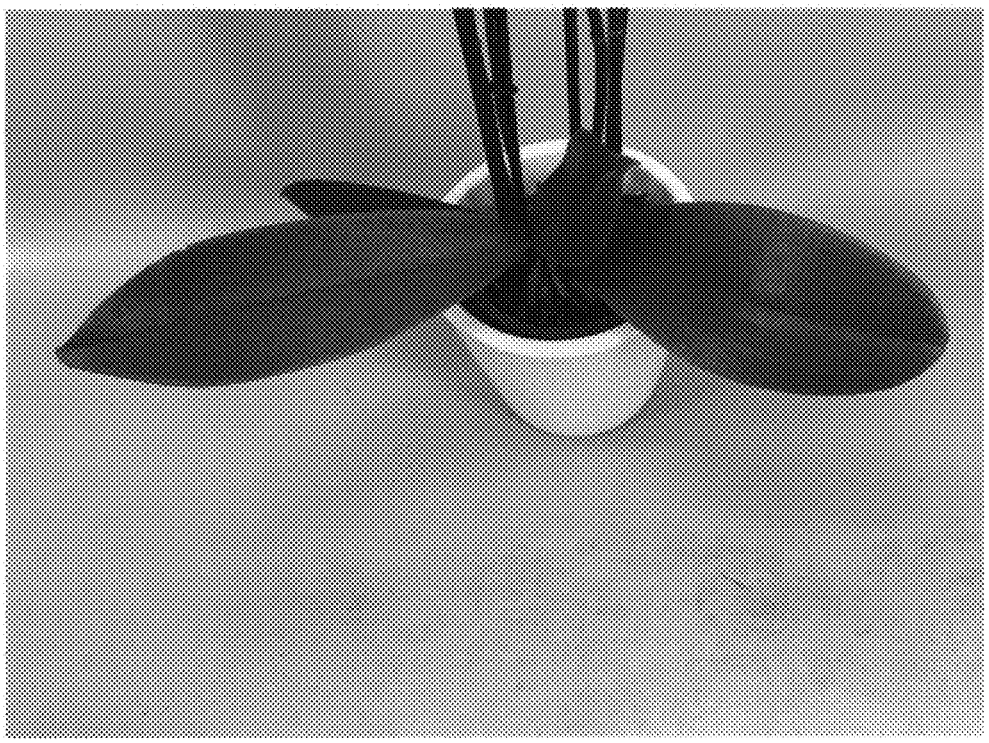
FIG. 3 shows an overhead view of the leaves of 'PHALGASCIJ'.

The following detailed description sets forth the distinctive characteristics of 'PHALGASCIJ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in January 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGASCIJ'.

Parentage:

*Female parent*.—*Phalaenopsis* cultivar '22286-05' (unpatented).

*Male parent*.—*Phalaenopsis* cultivar '01-3705' (unpatented).

Propagation:

*Type*.—Meristem tissue culture.

Roots:

*Root description*.—Greyed-green (between RHS 190B and 190C) colored roots with branching lateral roots having yellow-green (RHS 146D) colored root tips with a touch of purplish-red (RHS N77B).

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 40.0 cm to 45.0 cm.

*Width* (*measured from leaf tips*).—About 34.0 cm to 36.0 cm.

*Vigor*.—Strong.

Leaves:

*Mature leaves*.—Quantity per plant: 7 to 8 leaves are produced before flowering. Length (fully expanded): 19.0 cm to 22.0 cm. Width: 6.5 cm to 7.5 cm. Position of the broadest part of the leaf: Toward the apex. Shape: Oblong. Base shape: Moderately elongated. Apex: Unequal obtuse to acute. Leaf blade angle with the petiole (measured from the horizontal position): Between 20 degrees and 40 degrees. Leaf margin: Entire. Color: Upper surface: RHS 146A. Lower surface: RHS 146B with a touch of RHS N199B. Texture (both upper and lower surfaces): Smooth. Thickness: 2.0 mm to 2.3 mm. Variegation: Absent. Venation: Pattern: Parallel. Color of the midvein: Upper surface: RHS 146A. Lower surface: RHS N199B.

Peduncle:

*Quantity per plant*.—1 to 4.

*Number of flowers per peduncle*.—5 to 9.

*Length*.—40.0 cm to 45.0 cm.

*Diameter*.—5.0 mm to 5.5 mm.

*Strength*.—Strong.

*Aspect*.—Upright. to slightly pendent.

*Texture*.—Smooth.

*Color*.—Mix of brown (RHS 200C) and yellow-green (RHS 146C).

*Internode length*.—3.0 cm to 4.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 4.

*Inflorescence size*.—Height (from base to tip): 60.0 mm to 120.0 mm. The inflorescence starts at the base of the first flower and ends at the tip of the inflorescence. As shown in FIG. 1, the size of the flower is in the horizontal dimension and the size of the inflorescence is in the vertical dimension. The variety has a very short inflorescence.

*Flowering time*.—First flowers can be expected 10 to 11 months after planting in a 12-cm pot.

*Flower*.—Height: 66.0 mm to 71.0 mm. Diameter: 73.0 mm to 78.0 mm. Depth of lip: 20.0 mm to 22.0 mm.

*Flower longevity*.—On the plant: 10 to. 13 weeks.

*Flower shape*.—Flat.

*Fragrance*.—Absent.

*Flower bud*.—Average size: Large. Length: 23.0 mm to 25.0 mm. Width: 20.0 mm to 22.0 mm. Shape: Egg shaped. Color: Greenish-yellow (RHS 151A) with a touch of diluting red (RHS 182B).

*Petals*.—Arrangement: Open/free. Shape: Semi-circular. Apex: Emarginated asymmetric. Margin: Entire. Length (from base to tip): 34.0 mm to 36.0 mm. Width: 38.0 mm to 40.0 mm. Position of the broadest part of the petal: Toward the base. Color (when fully opened): Upper surface: Basic color: Orange-yellow (RHS 163B). Over color: Red stripes (RHS 181A). Lower surface: Basic color: Yellow (RHS 153D). Over color: Red stripes (RHS 181B to 181C) toward margin. Number of spots and stripes on the petals (upper surface): Medium stripes. Color of spots and stripes on the petals (upper surface): RHS 181A. Density of netting of the petals (upper surface): None. Color of the netting (upper surface): None.

*Dorsal sepal*.—Shape: Elliptic. Apex: Emarginated symmetric. Margin: Entire. Length (from base to tip): 37.0 mm to 39.0 mm. Width: 28.0 mm to 30.0 mm. Position of the broadest part of the dorsal sepals: At the middle. Color (when fully opened): Upper surface: Basic color: Brownish-orange (RHS N167A). Over color: Red stripes (RHS 181A). Lower surface: Basic color: Greenish-yellow (RHS 151B). Over color: Red stripes (RHS 181C) toward the margin. Number of spots and stripes on the dorsal sepals (upper surface): Medium to many stripes. Color of spots and stripes on the dorsal sepals (upper surface): RHS 181A. Density of netting of the dorsal sepals (upper surface): None. Color of the netting: None.

*Lateral sepals*.—Shape: Ovate. Apex: Obtuse symmetric. Margin: Entire. Length (from base to tip): 35.0 mm to 37.0 mm. Width: 28.0 mm to 30.0 mm. Position of the broadest part of the lateral sepals: Toward the base. Color (when fully opened): Upper surface: Basic color: Brownish-orange (RHS N167A). Over color: Red dots and stripes (RHS 184A). Lower surface: Basic color: Greenish-yellow (RHS 151B). Over color: Red stripes (RHS 184B). Number of spots and stripes on the lateral sepals (upper surface): Few dots at the base and medium to many stripes. Color of spots and stripes on the lateral sepals (upper surface): RHS 184A. Density of netting of the lateral sepals (upper surface): None. Color of the netting (upper surface): None.

*Labellum* (*lip*).—Whiskers: Present. Length of whiskers: 4.0 mm to 6.0 mm. Color of whiskers: Reddish-purple (RHS N78B). Pubescence on the lip: Absent.

*Lateral lobe*.—Shape: Type III (as described in the International Union for the Protection of New Varieties of Plants (UPOV) Test Guidelines for *Phalaenopsis*); oblong. Margin: Entire. Length: 12.0 mm to 14.0 mm. Width: 5.0 mm to 7.0 mm. Color: Upper surface: Light greenish-yellow (RHS 8B) at the base with red stripes (RHS 60A); reddish-purple (RHS N78A) toward the margin. Lower surface: White (RHS NN155C) at the base; reddish-purple (RHS N78B) toward the tip. Number of spots and stripes on the lateral lobe: Medium. Color of spots and stripes on the lateral lobe: RHS 60A. Density of netting of the lateral lobe: None. Color of the netting: None.

*Apical lobe*.—Shape: Elliptic. Margin: Entire. Length: 17.0 mm to 19.0 mm. Width: 16.0 mm to 18.0 mm. Color: Upper surface: Slightly yellow (RHS 9A) at the base; red (RHS 185A) and reddish-purple (RHS N78A) toward the whiskers. Lower surface: Yellowish-white (RHS 155B) in the middle; reddish-orange (RHS 178B) toward the margin on both sides; reddish-purple (RHS N78B) toward whiskers. Number of spots and stripes on the apical lobe: None. Color of spots and stripes on the apical lobe: None. Density of netting of the apical lobe: None. Color of the netting: None. Bump and ridge: Present.

*Callus*.—Average size: Small. Height: 4.0 mm to 5.0 mm. Length: 3.0 mm to 4.0 mm. Width: 3.0 mm to 4.0 mm. Color: Yellow (RHS 9A) with dark reddish-orange spots (RHS 178B).

Reproductive organs:

*Column*.—Length: 9.0 mm to 11.0 mm. Diameter: 5.0 mm to 6.0 mm. Color: Light reddish-purple (RHS N78D) at the base; white (RHS NN155C) toward the tip.

*Pollinia*.—Quantity: 2. Diameter: 0.8 mm to 1.0 mm. Color: Orange-yellow (RHS 24A).

*Ovary*.—Length: 14.0 mm to 16.0 mm. Diameter: 2.0 mm to 3.0 mm.

*Pedicel*.—Length: 38.0 mm to 40.0 mm. Diameter: 3.0 mm to 4.0 mm. Texture: Smooth. Color: Touch of reddish-brown (RHS 176B) at the base; light yellow-green (RHS 145C to 145D) with a hint of very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGASCIJ' differs from female parent plant '22286-05' (unpatented) in that 'PHALGASCIJ' has flowers with a striped pattern, elliptic apical lobes, small calluses, and columns that are light reddish-purple at the base and white toward the tip, whereas '22286-05' has flowers with a spotted pattern, rhombic apical lobes, very small calluses, and columns that are white.

'PHALGASCIJ' differs from male parent plant '01-3705' (unpatented) in that 'PHALGASCIJ' has elliptic apical lobes and small calluses, whereas '01-3705' has ovate apical lobes and medium calluses.

'PHALGASCIJ' is most similar to the commercial *Phalaenopsis* plants named 'PHALGURZON' (U.S. Plant Pat. No. 31,708) and 'PHALFYPCI' (U.S. Plant Pat. No. 26,961). 'PHALGASCIJ' differs from the commercial variety 'PHALGURZON' in that 'PHALGASCIJ' has elliptic apical lobes, whiskers that are reddish-purple, and columns that are light reddish-purple at the base and white toward the tip, whereas 'PHALGURZON' has trullate apical lobes, whiskers that are reddish-purple at the base and orange-yellow toward the tip, and columns that are light reddish-purple. Additionally, 'PHALGASCIJ' has narrower leaves than 'PHALGURZON'.

'PHALGASCIJ' differs from the commercial variety 'PHALFYPCI' in that 'PHALGASCIJ' has elliptic apical lobes and reddish-purple whiskers, whereas 'PHALFYPCI' has rhombic apical lobes and orange-yellow whiskers.

I claim:

1. A new and distinct variety of *Phalaenopsis* plant named 'PHALGASCIJ', substantially as described and illustrated herein.

* * * * *